(12) United States Patent
Drauz et al.

(10) Patent No.: US 6,225,482 B1
(45) Date of Patent: May 1, 2001

(54) PROCESS FOR THE ENANTIOSELECTIVE EPOXIDATION OF C=C DOUBLE BONDS

(75) Inventors: Karlheinz Drauz, Freigericht-Somborn (DE); Stan M. Roberts, Neston; John Skidmore, Liverpool, both of (GB)

(73) Assignee: Degussa-Huls Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/451,100

(22) Filed: Nov. 30, 1999

(30) Foreign Application Priority Data

Dec. 3, 1998 (DE) .............................. 198 55 858

(51) Int. Cl.⁷ .................................. C07D 303/32

(52) U.S. Cl. .......................... 549/525; 549/524; 549/529; 549/531

(58) Field of Search .................. 549/524, 525, 549/529, 531

(56) References Cited

PUBLICATIONS

Ray et al, Tet. Letters, vol. 40, pp. 1779–1782, Feb. 26, 1999.*

* cited by examiner

*Primary Examiner*—Bernard Dentz
(74) *Attorney, Agent, or Firm*—Pillsbury Winthrop LLP

(57) ABSTRACT

A process for the enantioselective epoxidation of C=C double bonds and use of the epoxides.

The present invention provides a process for the enantioselective epoxidation of compounds of the formula I

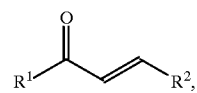

by means of a diastereomer and enantiomer enriched homopolyamino acid and an oxidizing agent. The epoxides prepared according to the invention are used as intermediates in organic syntheses.

19 Claims, No Drawings

PROCESS FOR THE ENANTIOSELECTIVE EPOXIDATION OF C=C DOUBLE BONDS

CROSS-REFERENCE TO RELATED APPLICATION

This application claims priority from German Application No. 198 55 858.9, filed on Dec. 3, 1998, the subject matter of which is hereby incorporated herein by reference.

BACKGROUND OF THE INVENTION

1. Field of the Invention

The present invention provides a process for the enantioselective epoxidation of C=C double bonds. In particular, the invention relates to the epoxidation of compounds of the general formula I

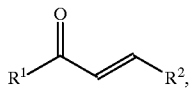

in which
$R^1$ and $R^2$, independently, represent $(C_1-C_{18})$-alkyl, $(C_2-C_{128})$-alkenyl, $(C_2-C_{18})$-alkynyl, $(C_6-C_{18})$-aryl, $(C_7-C_{19})$-aralkyl, $(C_3-C_{18})$-heteroaryl, $(C_4-C_{19})$-heteroaralkyl,
$(C_1-C_8)$-alkyl-$(C_6-C_{18})$-aryl,
$(C_1-C_8)$-alkyl-$(C_3-C_{19})$-heteroaryl, $(C_3-C_8)$-cycloalkyl,
$(C_1-C_8)$-alkyl-$(C_3-C_8)$-cycloalkyl,
$(C_3-C_8)$-cycloalkyl-$(C_1-C_8)$-alkyl,
wherein the groups mentioned above may be substituted once or several times with heteroatoms such as a halogen, $NR^3R^4$, $PO_{0-3}R^3R^4$, $OR^3$, $SR^3$, $SOR^3$, $SO_2R^3$, $SO_3R^3$ or groups such as $CO_2R^3$, $CONHR^3$ and one or more $CH_2$ groups may be substituted by heteroatoms such as $NR^3$, $PR^3$, O or S, $R^3$ and $R^4$, independently, represent H, $(C_1-C_{18})$-alkyl, $(C_2-C_8)$-alkenyl, $(C_6-C_{18})$-aryl, $(C_3-C_{18})$-heteroaryl, $(C_1-C_8)$-alkyl-$(C_6-C_{18})$-aryl,
$(C_1-C_8)$-alkyl-$(C_3-C_{19})$-heteroaryl, $(C_3-C_8)$-cycloalkyl, or
$(C_1-C_8)$-alkyl-$(C_3-C_8)$-cycloalkyl,
wherein the groups mentioned above may be substituted once or several times with a halogen, by means of a diastereomer and enantiomer enriched homopolyamino acid and an oxidizing agent.

2. Background Information

Enantioselective epoxidation reactions are important reactions for building up chiral intermediates for organic syntheses. In particular, the asymmetric epoxidation of allyl alcohols according to Sharpless et al. and manganese salt promoted enantioselective epoxidation according to Jacobsen et al. are well established in organic syntheses for the building up of chiral molecules (Sharpless et al., J. Am. Chem. Soc. 1980, 102, 5974; J. Am. Chem. Soc. 1987, 109, 5765; J. Org. Chem. 1986, 51, 1922; Jacobsen et al., J. Am. Chem. Soc. 1990, 112, 2801; J. Am. Chem. Soc. 1991, 113, 7063).

Another possibility for the asymmetric epoxidation of C=C double bonds has been disclosed in the reaction of chalcones with hydrogen peroxide in the presence of enantiomer enriched polyamino acids (Colonna et al., Org. Synth.; Mod. Trends, Proc. IUPAC Symp. 6th, 1986, 275; Julia et al., Angew. Chem., Int. Ed. Engel, 1980, 19, 929).

The methods of synthesis just mentioned all have the disadvantage that they can be applied to a relatively narrow range of substrates. For this reason, and because of the continuing research taking place in this area, there is a need to provide improved epoxidation procedures.

Two different variants of the Julia-Colonna epoxidation reaction, the two phase and the three phase variants, have been disclosed in the prior art to date (S. M. Roberts et al. Chem. Commun. 1998, 1159; WO 96/33183). The two phase variant makes use of an organic solvent and operates with oxidizing agents which are soluble in these solvents, in the presence of insoluble homopolyamino acids. The three phase variant uses water as the third phase, in addition to the water-insoluble organic solvent. Thus, water-soluble oxidizing agents can advantageously be used for the reaction; optionally in the presence of phase transfer catalysts.

From documents relating to the last-mentioned epoxidation reaction, however, it is clear that there are critical defects in this method of epoxidation with regard to its use in an industrial process, these being the occasionally low space/time yield (reaction times of the order of days) and the poor ee-values which are sometimes obtained for many substrates.

SUMMARY OF THE INVENTION

Therefore, the object of the present invention was to provide the possibility of oxidizing C=C double bonds using a method which is not inferior to the methods in the prior art with regard to the chiral induction effect, but which offers advantages with regard to the space/time yield, simplicity of application and economy when using the method on an industrial scale.

These and other objects which are not mentioned in detail, but which are produced readily and in an obvious manner from the prior art, are achieved by a process wherein the epoxidation reaction is performed in the presence of water and one or more organic solvents which are miscible with water.

As a result of the enantioselective epoxidation of compounds of the general formula I

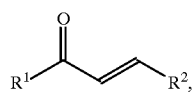

in which
$R^1$ and $R^2$, independently, represent $(C_1-C_{18})$-alkyl, $(C_2-C_{18})$-alkenyl, $(C_2-C_{18})$-alkynyl, $(C_6-C_{18})$-aryl, $(C_7-C_{19})$-aralkyl, $(C_3-C_{18})$-heteroaryl, $(C_4-C_{19})$-heteroaralkyl,
$(C_1-C_8)$-alkyl-$(C_6-C_{18})$-aryl,
$(C_1-C_8)$-alkyl-$(C_3-C_8)$-heteroaryl, $(C_3-C_8)$-cycloalkyl,
$(C_1-C_8)$-alkyl-$(C_3-C_8)$-cycloalkyl,
$(C_3-C_8)$-cycloalkyl-$(C_1-C_8)$-alkyl,
wherein the groups mentioned above may be substituted once or several times by heteroatoms such as a halogen, $NR^3R^4$, $PO_{0-3}R^3R^4$, $OR^3$, $SR^3$, $SOR^3$, $SO_2R^3$, $SO_3R^3$ or groups such as $CO_2R^3$, $CONHR^3$ or one or more $CH_2$ groups may be substituted by heteroatoms such as $NR^3$, $PR^3$, O or S, $R^3$ and $R^4$, independently, represent H, $(C_1-C_{18})$-alkyl, $(C_2-C_{18})$-alkenyl, $(C_6-C_{18})$-aryl, $(C_3-C_{18})$-heteroaryl, $(C_1-C_8)$-alkyl-$(C_6-C_{18})$-aryl, $(C_1-C_8)$-alkyl-$(C_3-C_{19})$-heteroaryl, $(C_3-C_8)$-cycloalkyl,
$(C_1-C_8)$-alkyl-$(C_3-C_8)$-cycloalkyl,
wherein the groups mentioned above may be substituted once or several times with a halogen,
by means of a diastereomer and enantiomer enriched homopolyamino acid and an oxidizing agent in such a way that epoxidation takes place in the presence of water and one or more solvents which are miscible with water, the desired highly enantiomer enriched epoxidised derivatives are obtained in a manner which was not readily predictable and in a relatively simple process with short reaction times and high yields. At the same time the method according to the invention enables the use of compounds in which the basic structure is not restricted exclusively to the chalcones used in the prior art.

In this reaction, DMF, acrylonitrile, DMSO, water-soluble alcohols or water-soluble ethers are preferably used as water-miscible organic solvents. The use of 1,2-dimethoxyethane (DME) is particularly preferred. The solvents may be used separately or as a mixture.

The monophase solvent mixture used as solvent in this method is responsible for the advantageous properties of this reaction variant. Therefore, this solvent system is not comparable to the classical 2/3-phase processes, since an organic solvent is used, as in the 3-phase process, but only a two-phase system is obtained during the reaction.

The choice of the ratio of water to organic solvent in order to produce these advantageous properties is relatively non-critical. A ratio of 10:1 to 1:10 may preferably be used. In particular, a ratio of 5:1 to 1:8 is used, quite specifically 1:1 to 1:5.

Compounds which may preferably be used as substrates of the general formula I, are those in which
$R^1$ represents $(C_1-C_{18})$-alkyl, $(C_2-C_{18})$-alkenyl,
$(C_6-C_{18})$-aryl, $(C_3-C_{18})$-heteroaryl,
$(C_1-C_8)$-alkyl-$(C_6-C_{18})$-aryl,
$(C_1-C_8)$-alkyl-$(C_3-C_{19})$-heteroaryl, $(C_3-C_8)$-cycloalkyl,
$(C_1-C_8)$-alkyl-$(C_3-C_8)$-cycloalkyl,
wherein the groups mentioned above may be substituted once or several times with a halogen or $NR^3R^4$ and
$R^2$ represents $(C_1-C_{18})$-alkyl, $(C_2-C_{18})$-alkenyl,
$(C_6-C_{18})$-aryl, $(C_3-C_{18})$-heteroaryl,
$(C_1-C_8)$-alkyl-$(C_6-C_{18})$-aryl,
$(C_1-C_8)$-alkyl-$(C_3-C_{19})$-heteroaryl, $(C_3-C_8)$-cycloalkyl,
$(C_1-C_8)$-alkyl-$(C_3-C_8)$-cycloalkyl,
wherein the groups mentioned above may be substituted once or several times with a halogen or $NR^3R^4$ and also
$R^3$ and $R^4$ are defined in the same way as above.

A variety of diastereomer and enantiomer enriched homopolyamino acids may be used to prepare the enantiomer enriched epoxides. Preferably, however, homopolyamino acids from the group polyneopentylglycine, polyleucine, polyisoleucine, polyvaline and polyalanine and also polyphenylalanine are used. From this group, polyneopentylglycine is generally preferred.

The chain length of the polyamino acid is chosen so that, on the one hand, chiral induction is not impaired during the reaction and, on the other hand, the costs of synthesizing the polyamino acid are not too great. The chain length of the homopolyamino acid is advantageously between 5 and 100, preferably 7 and 50 amino acids. In particular, a chain length of 10 to 40 amino acids is preferred.

The homopolyamino acids may be used in an unmodified form in the reaction. The embodiment in which the homopolyamino acids are cross-linked with polyfunctional amines or are extended by other organic polymers is preferred. 1,3-diaminopropane, propyleniminotetraamino dendrimers of the 1st generation or transverse cross-linked hydroxy- or amino-polystyrene (CLAMPS, commercially available) are advantageously used as cross-linking amines. Polyethylene glycol/polystyrene based nucleophilic compounds are suitable as polymeric extenders. These types of modified polyamino acids are described in Chem. Commun 1998, 1159 et seq. and Tetrahedron: Asymmetry 1997, 8, p. 3165 et seq.

Insoluble support materials are preferably those which are built up on the basis of silicon dioxide such as, for example, molecular sieves, silica gel or zeolites and also Celite 521® or Celite Hyflo Super Cell®, Wessalith® Day P. Silica gels with defined pore sizes such as, for example, CPC I or CPC II are also advantageous. Nitrocellulose or active carbon are also preferred as support materials.

The ratio of support material to polyamino acid is bounded by two limits. On the one hand, only a certain number of polyamino acids can be adsorbed on the insoluble support and, on the other hand, chiral induction dies down if there is less than 10 wt. % of polyamino acid to support material. The ratio is advantageously between 1:7 and 2:1 parts by wt., preferably 1:5 to 1:1 parts by wt.

The oxidizing agents used, which are advantageously introduced in a molar amount with respect to the compound being oxidized, preferably in a ratio of 1:1 to 1:2, are generally peroxides, peracids, an aqueous solution of $H_2O_2$ or inorganic oxidizing agents such as sodium perborate or sodium percarbonate, preferably $Na_2CO_3 \cdot 1.5\ H_2O_2$. Other oxidizing agents which can be used in this reaction are the compounds mentioned in Houben-Weyl vol. 4/1a+b, p. 59–319 and those mentioned in Oxidation in Organic Chemistry, Milos Hudlicky, ACS Monograph 186, Washington, DC 1990, p. 1–47.

The amount of catalyst to be used in this reaction may vary over a wide range. It is generally restricted by the concentration below which chiral induction begins to fall away or above which the use of an expensive catalyst is regarded as economically non-viable. In general, the molar ratio of catalyst to substrate is between 1:1 and 0.005:1. A catalyst ratio of 0.5:1 to 0.05:1 is particularly preferred.

The temperature at which epoxidation is performed should be between −30° C. and 80° C. The temperature should preferably be adjusted so that it is between −10° C. and 50° C., in particular between 15 and 30° C.

The pH which is set during the reaction can be chosen so that an excess of deprotonated $H_2O_2$, as compared to non-deprotonated $H_2O_2$, is present. On the other hand, the pH should not be so high, even during reaction, that the organic compounds used suffer any damage. The pH is preferably between 7 and 14, in particular between 7.5 and 13.

It may be of advantage to the invention if a phase transfer catalyst is added to the reaction mixture consisting of substrate, oxidizing agent, polyamino acid and solvent mixture. Preferred catalysts are any catalysts of this type which are of a cationic nature, in particular quaternary ammonium compounds such as Aliquat 336, Triton B, etc. Other catalysts are mentioned in Phase-Transfer Catalysis by C. M. Starks et al., Chapman & Hall London, 1990, p. 123–187.

The enantiomer enriched epoxides prepared in accordance with Claim 1 are preferably used as chiral intermediates in organic syntheses.

The homopolyamino acids to be used during epoxidation may be prepared by methods known from the prior art (Flisak et al., J. Org. Chem. 1993, 58, 6247). The method can be applied to both optical antipodes of the amino acids. The use of a specific antipode of a polyamino acid correlates with the stereochemistry of the epoxide, i.e. a poly-L-amino acid leads to the optical antipode of the epoxide which is obtained with a poly-D-amino acid.

It has been shown that treatment of the polymeric catalyst prior to use with basic aqueous media, as in EP 0 403 252 A2, can reduce the rate of reaction in the epoxidation reaction still further.

In the case of the reaction according to the present invention, the procedure is generally such that the homopolyamino acid to be used, or modified derivatives such as cross-linked, polymer-extended homopolyamino acids or homopolyamino acids adsorbed onto insoluble supports, is/are suspended in the solvent mixture according to the invention, then the oxidizing agent is added, the pH is adjusted and finally the substrate of the general formula I is added. It is not essential to follow the sequence of working steps, but the substrate should preferably be added as the last component to the mixture in order not to allow unwanted non-induced epoxidation to take place at the start of the reaction, when no catalyst has yet been added, because this produces product ee values which are too low.

The reaction mixtures are worked up using processes which are familiar to a person skilled in the art. The soluble epoxide is separated in an advantageous manner by filtering off the polyamino acid and is then worked up in an aqueous medium. If required, chromatography on silica gel may then be performed for purification purposes.

It has been shown that the catalyst can be recycled and used again in the reaction. In this connection, the use of polymer-extended or cross-linked polyamino acids or polyamino acids which are adsorbed onto insoluble supports are particularly preferred because they are easier to handle and can be filtered. They do not block the pores of membranes and filters like the free polyamino acids. Thus, these types of modified catalysts can also be extremely advantageous in an enzyme/membrane reactor (C. Wandrey in Enzymes as Catalysts in Organic Synthesis, Ed.: M. Schneider, Dordrecht Riedel 1986, 263–284) or a tubular reactor such as, for instance, a chromatography column, which enables a continuous or quasi-continuous mode of operation for the reaction which is most preferred for an industrial process.

The results of different methods applied to a standard operation, the oxidation of chalcone to an epoxychalcone, are compared in the following, using poly-L-leucine-CLAMPS (CLAMPS: cross-linked-amino-modified-poly styrene) as the catalyst (Scheme 1).

Scheme 1

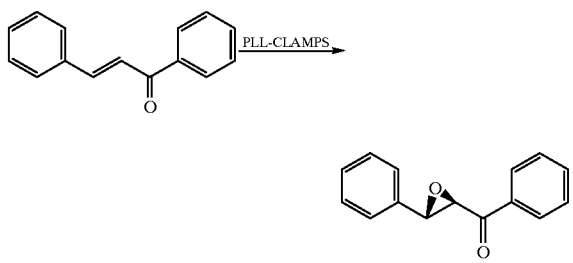

| Condition Cat. PLL-CLAMPS | Reaction time [h] | Conversion[b] [%] | ee value[) [%] |
|---|---|---|---|
| 3-phase Toluene/NaOH/H$_2$O$_2$[c) | 24 | 71 | 68 |
| 2-phase DABCO-H$_2$O$_2$/MTBE[a) | 0.33 | 97 | 98 |
| NaCO$_3$.1.5 H$_2$O$_2$/H$_2$O/ DME | 0.33 | 100 | 96 |

Conditions according to table

[a)]cf. Chem. Commun 1998, 1159;
[b)]chiral HPLC
[c)]EP 403 252

As can be seen from the results, the reaction times for the method according to the invention are much less than that given for the 3-phase variant. The results according to the invention and those for the 2-phase variant are equivalent. However, the use of an expensive auxiliary base (e.g. DABCO or DBU), which is inevitable in 2-phase method, is a disadvantage on a large scale. In addition, it has been shown that, when scaling-up the 2-phase variant, the ee value drops with increasing amount of substrate used per unit weight of catalyst. A similar effect was not observed with the method according to the invention (Scheme 2).

Scheme 2

| Amount of chalcone per | 2-phase | | according to the invention | |
|---|---|---|---|---|
| 100 mg cat. | Yield (%) | ee (%) | Yield (%) | ee (%) |
| 50 mg | 98 | 97 | 99 | 95 |
| 300 mg | 92 | 88 | 87 | 95 |

In addition, it has been demonstrated that even protected alcohols such as III are converted using the method according to the invention.

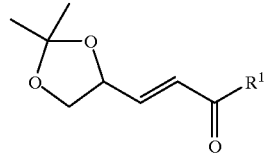

III

The epoxidation of these derivatives has not hitherto been disclosed in the prior art and is therefore all the more surprising.

Due to shortening the reaction times, it is now no longer necessary to stabilize the oxidizing agents used in any way at all. With reaction times from the prior art, in particular for the 3-phase variant which are of the order of days, chelating agents frequently had to be added to the reaction mixture because the oxidizing agents were gradually decomposed in the presence of heavy metal ions. The post-addition of oxidizing agent was also required in order to shift the reaction satisfactorily to completion. None of these procedures is required with the new process. This is especially advantageous with regard to its use on an industrial scale, since the amounts of essential and expensive starting materials can be reduced.

The process according to the invention, as described above, also has critical advantages as compared with the 2-phase procedure, in particular with regard to application in the industrial sector.

Furthermore, the invention therefore increases the attractiveness of the use of this reaction on an industrial scale because the normally long reaction times and the poor yields when performed on a large scale, which contribute to the intrinsic costs of the product, have been improved to acceptable values. This was extremely surprising and is not obvious from any suggestion in the prior art.

A person skilled in the art will understand the expression homopolyamino acid to mean polymers based on amino acids from one source. However, in the context of the invention, the homopolyamino acids used may also be copolymers of different amino acids in which, however, domains which bring about chiral induction should consist of standardised amino acids. In addition, the expression homopolyamino acids also applies to polymers built up from heterochiral amino acids. Again, the domains which bring about chiral induction should be built up from a stereochemically standardized sequence of amino acids.

In the context of the invention, a $(C_1-C_{18})$-alkyl group is understood to be a group with 1 to 18 saturated carbon atoms and any type of branched structure at all. The following groups are included in this group: methyl, ethyl, n-propyl, isopropyl, n-butyl, isobutyl, sec-butyl, tert-butyl, pentyl, hexyl etc. A $(C_1-C_8)$-alkyl group describes a group as defined above, but with 1 to 8 carbon atoms.

A $(C_2-C_{18})$-alkenyl group has the features mentioned above for a $(C_1-C_{18})$-alkyl group, wherein at least one double bond must be present within the group.

A $(C_2-C_{18})$-alkynyl group has the features mentioned above for a $(C_1-C_{18})$-alkyl group, wherein at least one triple bond must be present within the group.

A $(C_6-C_{18})$-aryl group is understood to be an aromatic group with 6 to 18 carbon atoms. This includes, in particular, substituents such as phenyl, naphthyl, anthryl, phenanthryl or biphenyl groups.

A $(C_7-C_{19})$-aralkyl group consists of a $(C_6-C_{18})$-aryl group bonded to the molecule via a $(C_1-C_8)$-alkyl group.

In the context of the invention, a $(C_3-C_{18})$-heteroaryl group designates a five, six or seven-membered aromatic ring system consisting of 3 to 18 carbon atoms which contains heteroatoms, such as, for example, nitrogen, oxygen or sulfur, in the ring. The following in particular are regarded as these types of heteroaromatic groups: 1-, 2-, 3-furyl, 1-, 2-, 3-pyrrolyl, 1-,2-,3-thienyl, 2-, 3-, 4-pyridyl, 2-, 3-, 4-, 5-, 6-, 7-indolyl, 3-, 4-, 5-pyrazolyl, 2-,4-, 5-imidazolyl, acridinyl, quinolinyl, phenanthridinyl, 2-, 4-, 5-, 6-pyrimidinyl, 4-, 5-, 6-, 7-(1-aza)-indolizinyl.

A $(C_4-C_{19})$-heteroaralkyl group is understood to be a heteroaromatic system corresponding to the $(C_7-C_{19})$-aralkyl group.

Furthermore, in the context of the invention, a $(C_3-C_8)$-cycloalkyl group designates a group from the group of cyclic alkyl groups with 3 to 8 carbon atoms and optionally any branched structure at all. This group includes the following in particular: cyclopropyl, cyclobutyl, cyclopentyl, cyclohexyl, cycloheptyl. One or more double bonds may be present in these groups.

A halogen is understood to be fluorine, chlorine, bromine or iodine.

In the context of the invention, the expression enantiomer enriched is understood to mean that the proportion of one enantiomer, mixed with its optical antipode, is within the range >50% to <100%.

In the context of the invention, the expression diastereomer enriched is understood to mean that the proportion of one diastereomer, mixed with its other diastereomer, is within the range >50% to <100%.

DETAILED DESCRIPTION OF THE INVENTION

Examples

Epoxidation with PLL

Sodium percarbonate (0.36 mmol) is added to a stirred suspension of chalcone (0.24 mmol) and PLL-CLAMPS (100 mg, Chem. Commun. 1998, 1159) in DME (0.5 cm$^3$) and water (0.5 cm$^3$), and the mixture is stirred for 20 min at RT. Then a portion is removed and analysed using HPLC (Chiralak AD column, 10% EtOH in hexane, 254 nm, 1.0 ml/min flowrate), after filtration.

Retention times for the enantiomeric epoxides: 15.9 (main enantiomer) and 23.7

For results, see Scheme 1.

Publications cited herein are hereby incorporated by reference.

What is claimed is:

1. A process for the enantioselective epoxidation of compounds of the general formula (I)

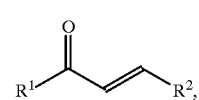

in which

R$^1$ and R$^2$, independently, represent $(C_1-C_{18})$-alkyl, $(C_2-C_{18})$-alkenyl, $(C_2-C_{18})$-alkynyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, wherein the groups mentioned above may be substituted once or several times with heteroatoms such as a halogen, NR$^3$R$^4$, PO$_{0-3}$R$^3$R$^4$, OR$^3$, SR$^3$, SOR$^3$, SO$_2$R$^3$, SO$_3$R$^3$ or groups such as CO$_2$R$^3$, CONHR$^3$ and one or more CH$_2$ groups may be substituted by heteroatoms such as NR$^3$, PR$^3$, O or S, R$^3$ and R$^4$, independently, represent H, $(C_1-C_{18})$-alkyl, $(C_2-C_{18})$-alkenyl, $(C_6-C_{18})$-aryl, $(C_3-C_{18})$-heteroaryl, $(C_1-C_8)$-alkyl-$(C_6-C_{18})$-aryl, $(C_1-C_8)$-alkyl-$(C_3-C_{19})$-heteroaryl, $(C_3-C_8)$-cycloalkyl, $(C_1-C_8)$-alkyl-$(C_3-C_8)$-cycloalkyl, wherein the groups mentioned above may be substituted once or several times with a halogen, by means of a diastereomer and enantiomer enriched homopolyamino acid and an oxidizing agent, wherein the epoxidation reaction is performed in the presence of water and one or more organic solvents which are miscible with water.

2. A process according to claim 1 wherein DMF, acrylonitrile, DMSO, water-soluble alcohols or water-soluble ethers is used as an organic solvent.

3. A process according to claim 2 wherein DME is used as an organic solvent.

4. A process according to claim 3, wherein the ratio of water to DME is 10:1 to 1:10.

5. A process according to claim 4 wherein the ratio is 5:1 to 1:8.

6. A process according to claim 1, wherein compounds of the general formula (I)
in which $R^1$ represents $(C_1-C_{18})$-alkyl, $(C_2-C_{18})$-alkenyl, $(C_6-C_{18})$-aryl, $(C_3-C_{18})$-heteroaryl, $(C_1-C_8)$-alkyl-$(C_6-C_{18})$-aryl, $(C_1-C_8)$-alkyl-$(C_3-C_{19})$-heteroaryl, $(C_3-C_8)$-cycloalkyl, $(C_1-C_8)$-alkyl-$(C_3-C_8)$-cycloalkyl,
wherein the groups mentioned above may be substituted once or several times with a halogen or $NR^3R^4$ and $R^2$ represents $(C_1-C_{18})$-alkyl, $(C_2-C_{18})$-alkenyl, $(C_6-C_{18})$-aryl, $(C_3-C_8)$-heteroaryl, $(C_1-C_8)$-alkyl-$(C_6-C_{18})$-aryl, $(C_1-C_8)$-alkyl-$(C_3-C_{19})$-heteroaryl, $(C_3-C_8)$-cycloalkyl, $(C_1-C_8)$-alkyl-$(C_3-C_8)$-cycloalkyl,
wherein the groups mentioned above may be substituted once or several times with a halogen or $NR^3R^4$ and $R^3$ and $R^4$ are defined in the same way as above, are converted.

7. A process according to claim 1, wherein a compound from the group polyneopentylglycine, polyleucine, polyisoleucine, polyvaline, polyphenylalanine and polyalanine is used as the homopolyamino acid.

8. A process according to claim 1, wherein the homopolyamino acid has a chain length of 5 to 100 amino acids.

9. A process according to claim 8, wherein the homopolyamino acid has a chain length of 7 to 50 amino acids.

10. A process according to claim 1, wherein the homopolyamino acid is present, during epoxidation, in the free form, cross-linked form or extended with polymers or adsorbed on immobilized supports.

11. A process according to claim 1, wherein a peroxide, a peracid, an aqueous solution of $H_2O_2$ or inorganic oxidizing agent is used as an oxidizing agent.

12. A process according to claim 11, wherein sodium percarbonate or sodium perborate is used as an oxidizing agent.

13. A process according to claim 1, wherein the catalyst ratio lies within the range 1:1 to 0.005:1, with respect to the substrate being converted.

14. A process according to claim 13, wherein the ratio lies within the range of 0.5:1 to 0.05:1, with respect to the substrate being converted.

15. A process according to claim 1, wherein the temperature during epoxidation is between 15° C. and 30° C.

16. A process according to claim 1, wherein epoxidation is performed in the pH range from 7 to 14.

17. A process according to claim 16, wherein the pH range is 7.5 to 13.

18. A process according to claim 1, wherein a phase transfer catalyst is added to the epoxidation mixture consisting of substrate, oxidizing agent, polyamino acid and solvent mixture.

19. A process for the synthesis of an organic compound comprising formation of the epoxide according to claim 1 and further reacting said epoxide as a chiral intermediate to obtain the organic compound.

* * * * *